(12) United States Patent
Yokoi et al.

(10) Patent No.: US 11,098,007 B2
(45) Date of Patent: Aug. 24, 2021

(54) CRYSTAL OF AMINO ACID SALT OF 3-HYDROXYISOVALERIC ACID AND PRODUCTION METHOD THEREOF

(71) Applicants: KYOWA HAKKO BIO CO., LTD., Tokyo (JP); OTSUKA PHARMACEUTICAL FACTORY, INC., Naruto (JP)

(72) Inventors: Tomoya Yokoi, Tokyo (JP); Hiroshi Nagano, Tokyo (JP); Takayuki Shimizu, Naruto (JP)

(73) Assignees: KYOWA HAKKO BIO CO., LTD., Tokyo (JP); OTSUKA PHARMACEUTICAL FACTORY, INC., Naruto (JP)

( * ) Notice: Subject to any disclaimer, the term of this patent is extended or adjusted under 35 U.S.C. 154(b) by 0 days.

(21) Appl. No.: 16/311,061

(22) PCT Filed: Jun. 23, 2017

(86) PCT No.: PCT/JP2017/023174
§ 371 (c)(1),
(2) Date: Dec. 18, 2018

(87) PCT Pub. No.: WO2017/222043
PCT Pub. Date: Dec. 28, 2017

(65) Prior Publication Data
US 2019/0210958 A1 Jul. 11, 2019

(30) Foreign Application Priority Data
Jun. 24, 2016 (JP) .............................. JP2016-125280

(51) Int. Cl.
| | | |
|---|---|---|
| C07C 227/42 | (2006.01) | |
| C07C 229/26 | (2006.01) | |
| C07C 51/41 | (2006.01) | |
| C07C 59/01 | (2006.01) | |
| C07C 51/43 | (2006.01) | |
| C07C 277/06 | (2006.01) | |
| C07C 279/14 | (2006.01) | |

(52) U.S. Cl.
CPC ............ *C07C 227/42* (2013.01); *C07C 51/41* (2013.01); *C07C 51/43* (2013.01); *C07C 59/01* (2013.01); *C07C 229/26* (2013.01); *C07C 277/06* (2013.01); *C07C 279/14* (2013.01); *C07B 2200/13* (2013.01)

(58) Field of Classification Search
CPC ........ C07C 51/41; C07C 51/43; C07C 227/42
USPC ....................................................... 562/554
See application file for complete search history.

(56) References Cited

U.S. PATENT DOCUMENTS

| | | |
|---|---|---|
| 4,579,955 A | 4/1986 | Lammerant et al. |
| 5,360,613 A | 11/1994 | Nissen |
| 6,031,000 A | 2/2000 | Nissen et al. |
| 6,248,922 B1 | 6/2001 | McCoy et al. |
| 9,598,344 B2 | 3/2017 | Long et al. |
| 2002/0010332 A1 | 1/2002 | Vollmuller et al. |
| 2004/0143136 A1 | 7/2004 | Heyl-Frank et al. |
| 2004/0176449 A1 | 9/2004 | Abraham et al. |
| 2013/0012565 A1 | 1/2013 | Tung et al. |
| 2014/0256980 A1 | 9/2014 | Li |
| 2015/0005507 A1 | 1/2015 | Matoba et al. |
| 2018/0327344 A1 | 11/2018 | Yokoi et al. |

FOREIGN PATENT DOCUMENTS

| | | |
|---|---|---|
| CN | 1434025 A | 8/2003 |
| JP | S57-128653 A | 8/1982 |
| JP | S58-201746 A | 11/1983 |
| JP | H08-501777 A | 2/1996 |
| JP | 2002-053583 A | 2/2002 |
| JP | 2002-518440 A | 6/2002 |
| JP | 2014-513046 A | 5/2014 |
| JP | 2015-028006 A | 2/2015 |
| WO | WO 2013/025775 A1 | 2/2013 |
| WO | WO 2014/166273 A1 | 10/2014 |
| WO | WO 2017/086447 A1 | 5/2017 |

OTHER PUBLICATIONS

Brittain "Polymorphism in pharmaceutical solids" Marcel Dekker, p. 178-179, 185,219, (1999).*
Michaëlsson et al., "Long term calcium intake and rates of all cause and cardiovascular mortality: community based prospective longitudinal cohort study," *BMJ*, 346: f228 (2013).
Nissen et al., "Effect of leucine metabolite β-hydroxy-β-methylbutyrate on muscle metabolism during resistance-exercise training," *J. Appl. Physiol.*, 81(5): 2095-2104 (1996).
Wilson et al., "Effects of beta-hydroxy-beta-methylbutyrate (HMB) on exercise performance and body composition across varying levels of age, sex, and training experience: A review," *Nutr. Metab. (Lond.)*, 5: 1 (2008).
Wilson et al., "International Society of Sports Nutrition Position Stand: beta-hydroxy-beta-methylbutyrate (HMB)," *J. Int. Soc. Sports Nutr.*, 10(1): 6 (2013).
Japanese Patent Office, International Search Report in International Patent Application No. PCT/JP2017/023174 (dated Sep. 19, 2017).
Japanese Patent Office, International Preliminary Report on Patentability in International Patent Application No. PCT/JP2017/023174 (dated Dec. 25, 2018).

(Continued)

*Primary Examiner* — Ana Z Muresan
(74) *Attorney, Agent, or Firm* — Leydig, Voit & Mayer, Ltd.

(57) ABSTRACT

An object of the present invention is to provide a crystal of an amino acid salt of HMB which is easy to handle and has high solubility, and to provide a method for producing the same. According to the present invention, the crystal of an amino acid salt of HMB can be precipitated by dissolving an amorphous amino acid salt of HMB in a solvent containing alcohol and stirring or allowing the solvent to left stand. In addition, the crystal of an amino acid salt of HMB can be precipitated by concentrating an aqueous HMB solution of an amino acid salt which has a pH of 2.5 to 11.0.

20 Claims, 8 Drawing Sheets

(56) References Cited

OTHER PUBLICATIONS

The Chemical Society of Japan, 4th Edition Jikken Kagaku Koa 1 Kihon Sosa I, pp. 184-186 (Maruzen Co., Ltd., 1990), Int'l Search Report in PCT/JP2016/084288 (dated Jan. 10, 2017).

European Patent Office, Extended European Search Report in European Patent Application No. 16866447.2 (dated May 9, 2019).

Japanese Patent Office, International Search Report in International Patent Application No. PCT/JP2016/084288 (dated Jan. 10, 2017).

Japanese Patent Office, International Preliminary Report on Patentability in Japanese Patent Application No. PCT/JP2016/084288 (dated May 22, 2018).

Hirayama, "Handbook for Production of Crystal of Organic Compound: Principle and Know-How," Sections 1.10 and 2.2.3, pp. 14-15 and 20-21 (Jul. 25, 2008).

Indian Patent Office, Hearing Notice in Indian Patent Application No. 201847048269 (dated Mar. 30, 2021).

Japanese Patent Office, Notice of Reasons for Refusal in Japanese Patent Application No. 2018-524179 (dated Jun. 14, 2021).

\* cited by examiner

US 11,098,007 B2

CRYSTAL OF AMINO ACID SALT OF 3-HYDROXYISOVALERIC ACID AND PRODUCTION METHOD THEREOF

CROSS-REFERENCE TO RELATED APPLICATIONS

This patent application is the U.S. national phase of International Patent Application No. PCT/JP2017/023174, filed Jun. 23, 2017, which claims the benefit of Japanese Patent Application No. 2016-125280, filed on Jun. 24, 2016, which are incorporated by reference in their entireties herein.

TECHNICAL FIELD

The present invention relates to a crystal of an amino acid salt of a 3-hydroxyisovaleric acid (β-hydroxy-β-methylbutyrate) (hereinafter, referred to as HMB) which is useful, for example, as a product, a raw material, an intermediate or the like of health food, medicines, cosmetics, or the like, and a method for producing the crystal.

BACKGROUND ART

HMB is useful, for example, as a product, a raw material, an intermediate or the like of health food, medicines, cosmetics, or the like. HMB is an organic acid obtained by leucine metabolism in the body and is considered to have effect of anabolizing muscle or preventing degradation of muscle (Non-Patent Documents 1 and 2).

From a commercial perspective, HMB is distributed in the market only in the form of either a free carboxylic acid or a calcium salt. Particularly, in supplement/health food applications, a calcium salt is used in most cases because the calcium salt is a powder which is excellent in handling (Non-Patent Document 3). Patent Document 4 discloses that a crystal of an arginine salt is obtained but does not disclose properties of the crystal obtained.

Calcium is an essential mineral playing a role in the bone formation, nerve activity, muscle movement, and the like. However, it has been recently reported that a calcium overdose leads to an increased risk of death due to cardiovascular disease or ischemic heart disease (Non-Patent Document 4).

RELATED ART

Patent Document
 [Patent Document 1] WO 2014/166273
 [Patent Document 2] U.S. Pat. No. 6,248,922
 [Patent Document 3] WO 2013/025775
 [Patent Document 4] U.S. Patent Application Publication No. 2004/0176449
 [Patent Document 2] U.S. Pat. No. 6,248,922
 [Patent Document 3] WO 2013/025775
 [Patent Document 4] U.S. Patent Application No. 2004/0176449

Non-Patent Document

[Non-Patent Document 1] Journal of Applied Physiology, Vol. 81, p 2095, 1996
[Non-Patent Document 2] Nutrition & Metabolism, Vol. 5, p 1, 2008
[Non-Patent Document 3] Journal of the International Society of Sports Nutrition Vol. 10, p 6, 2013
[Non-Patent Document 4] The BMJ., Vol. 346, p 228, 2013

DISCLOSURE OF INVENTION

Problems to be Solved by the Invention

In the pharmaceutical preparation field, there is a problem that calcium derived from a calcium salt binds to another component such as phosphate to form an insoluble salt, and a high-concentration solution cannot be prepared. Patent Documents 1 to 3, Patent Document 1, and Patent Document 4 disclose a method for producing calcium salt of HMB (Patent Document 1 to 3), magnesium salt of HMB (Patent Document 1), and arginine salt of HMB (Patent Document 4), respectively, but a crystal cannot be obtained by any methods. That is, there is no known crystal for any salt forms, and an industrially useful crystal of an HMB salt and a production method thereof are demanded.

An object of the present invention is to provide a crystal of an amino acid salt of HMB, which is excellent in solubility and easy to handle, and to provide a production method thereof.

Means for Solving the Problems

The present invention relates to the following (1) to (25)
(1) A crystal of an amino acid salt of a 3-hydroxyisovaleric acid (hereinafter referred to as HMB).
(2) The crystal described in (1) above, wherein the amino acid salt of HMB is a basic amino acid salt of HMB.
(3) The crystal described in (2) above, wherein the basic amino acid salt of HMB is arginine salt of HMB.
(4) The crystal described in (2) above, wherein the basic amino acid salt of HMB is lysine salt of HMB.
(5) The crystal described in (2) above, wherein the basic amino acid salt of HMB is ornithine salt of HMB.
(6) The crystal described in (3) above, wherein in powder X-ray diffraction, the crystal has peaks at diffraction angles (2θ) of 7.5±0.2°, 14.5±0.2°, 15.1±0.2°, 19.2±0.2°, and 20.2±0.2°.
(7) The crystal described in (6) above, wherein in powder X-ray diffraction, the crystal further has peaks at diffraction angles (2θ) of 11.6±0.2°, 12.7±0.2°, 17.9±0.2°, 21.5±0.2°, and 23.3±0.2°.
(8) The crystal described in (7) above, wherein in powder X-ray diffraction, the crystal further has peaks at diffraction angles (2θ) of 19.6±0.2°, 21.9±0.2°, 25.2±0.2°, 25.5±0.2°, and 33.6±0.2°.
(9) The crystal described in (4) above, wherein in powder X-ray diffraction, the crystal has peaks at diffraction angles (2θ) of 8.5±0.2°, 17.0±0.2°, 18.1±0.2°, 18.5±0.2°, and 19.5±0.2°.
(10) The crystal described in (9) above, wherein in powder X-ray diffraction, the crystal further has peaks at diffraction angles (2θ) of 22.2±0.2°, 25.5±0.2°, 25.8±0.2°, 26.6±0.2°, and 34.4±0.2°.
(11) The crystal described in (10) above, wherein in powder X-ray diffraction, the crystal further has peaks at diffraction angles (2θ) of 4.8±0.2°, 20.4±0.2°, 31.0±0.2°, 33.8±0.2°, and 36.5±0.2°.
(12) The crystal described in (5) above, wherein in powder X-ray diffraction, the crystal has peaks at diffraction angles (2θ) of 5.1±0.2°, 14.0±0.2°, 15.3±0.2°, 20.4±0.2°, and 21.9±0.2°.
(13) The crystal described in (12) above, wherein in powder X-ray diffraction, the crystal further has peaks at diffraction angles (2θ) of 16.4±0.2°, 16.8±0.2°, 19.4±0.2°, 21.4±0.2°, and 25.5±0.2°.

(14) The crystal described in (13) above, wherein in powder X-ray diffraction, the crystal further has peaks at diffraction angles (2θ) of 10.9±0.2°.
(15) A method for producing a crystal of an amino acid salt of HMB, the method comprising a step of dissolving an amorphous amino acid salt of HMB in a solvent containing alcohol, a step of precipitating a crystal of an amino acid salt of HMB by stirring or allowing the solvent to left stand, and a step of collecting a crystal of an amino acid salt of HMB from the solvent.
(16) A method for producing a crystal of an amino acid salt of HMB, the method comprising a step of concentrating an aqueous HMB solution containing an amino acid-containing compound and having a pH of 2.5 to 11.0 to precipitate a crystal of an amino acid salt of HMB, and a step of collecting a crystal of an amino acid salt of HMB from the aqueous solution.
(17) The production method described in (16) above, wherein the step of precipitating a crystal of an amino acid salt of HMB includes a step of adding or adding dropwise at least one solvent selected from the group consisting of alcohol, nitrile, and ketone.
(18) The production method described in (15) or (17) above, wherein the alcohol is at least one alcohol selected from the group consisting of C1 to C6 alcohols.
(19) The production method described in (17) or (18) above, wherein the nitrile is acetonitrile.
(20) The production method described in any one of (17) to (19) above, wherein the ketone is at least one ketone selected from the group consisting of acetone, methyl ethyl ketone, methyl isobutyl ketone, and diethyl ketone.
(21) The production method described in any one of (15) to (20) above, wherein the amino acid salt of HMB is a basic amino acid salt of HMB.
(22) The production method described in (21) above, wherein the basic amino acid salt of HMB is arginine salt of HMB, lysine salt of HMB, or ornithine salt of HMB.
(23) The crystal described in (5) above, wherein in powder X-ray diffraction, the crystal has peaks at diffraction angles (2θ) of 4.9±0.2°, 5.2±0.2°, 5.5±0.2°, 10.9±0.2° and 15.5±0.2°.
(24) The crystal described in (23) above, wherein in powder X-ray diffraction, the crystal further has peaks at diffraction angles (2θ) of 15.9±0.2°, 16.4±0.2°, 17.4±0.2°, 19.2±0.2°, and 20.4±0.2°.
(25) The crystal described in (24) above, wherein in powder X-ray diffraction, the crystal further has peaks at diffraction angles (2θ) of 20.8±0.2°, 21.3±0.2°, 21.8±0.2°, 22.2±0.2°, and 22.8±0.2°.

Effects of the Invention

According to the present invention, a crystal of an amino acid salt of HMB, which is easy to handle, and a production method thereof are provided. The crystal of an amino acid salt of HMB of the present invention is a salt crystal having superiority such as exhibiting high solubility, not forming an insoluble salt, and not inducing electrolyte abnormality, as compared to a calcium salt of HMB. In addition, the crystal of an amino acid salt of HMB of the present invention has high solubility and the excellent effect of improving flavor as compared to a calcium salt of HMB.

EMBODIMENTS FOR CARRYING OUT THE INVENTION

1. Crystal of Present Invention

Figure 1:
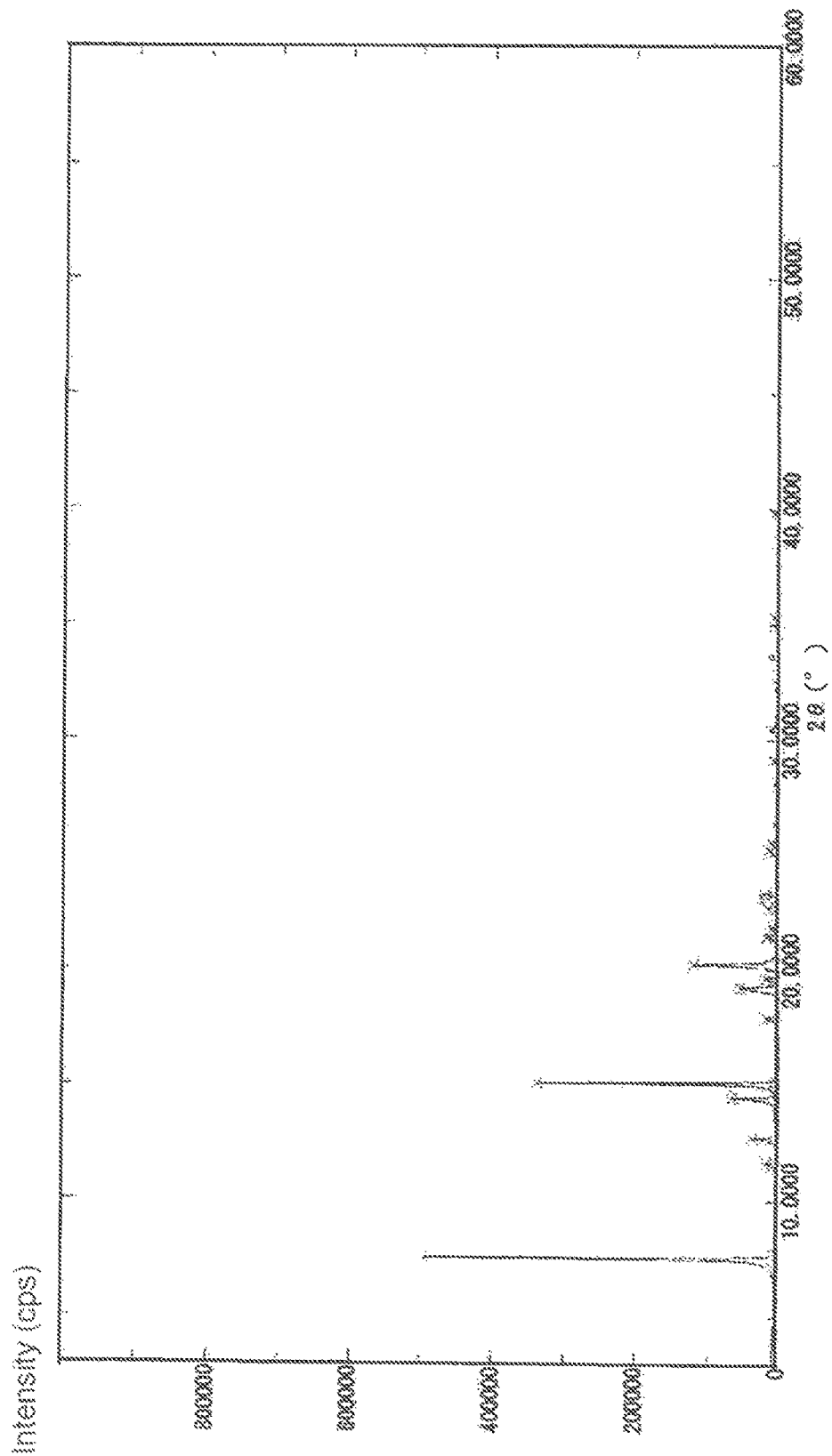
FIG. 1 illustrates the results of powder X-ray diffraction of a seed crystal of arginine salt nonhydrate of HMB obtained in Example 2.

A crystal of the present invention is a crystal of an amino acid salt of HMB (hereinafter referred to as "the crystal of the present invention" in some cases). Examples of the crystal of an amino acid salt of HMB preferably include a crystal of a basic amino acid salt of HMB, more preferably a crystal of arginine salt of HMB, a crystal of lysine salt of HMB, a crystal of histidine salt of HMB, and a crystal of ornithine salt of HMB, and most preferably a crystal of arginine salt of HMB, a crystal of lysine salt of HMB, and a crystal of ornithine salt of HMB.

The crystal of the present invention can be confirmed to be a crystal of HMB by the method using HPLC described in analysis examples later. As an amino acid in the crystal of the present invention, any one of an L form and a D form may be used, but the L form is preferable.

The crystal of the present invention can be confirmed to be a crystal of an amino acid salt by measuring the amino acid content in the crystal by using HPLC described in the analysis examples later.

For example, the crystal of the present invention can be confirmed to be a crystal of a mono-arginine salt by the fact that the arginine content in the crystal is generally 59.6±5.0 wt %, preferably 59.6±4.0 wt %, and most preferably 59.6±3.0 wt %.

For example, the crystal of the present invention can be confirmed to be a crystal of a monolysine salt by the fact that the lysine content in the crystal is generally 55.3±5.0 wt %, preferably 55.3±4.0 wt %, and most preferably 55.3±3.0 wt %.

For example, the crystal of the present invention can be confirmed to be a crystal of a mono-ornithine salt by the fact that the ornithine content in the crystal is generally 52.8±5.0 wt %, preferably 52.8±4.0 wt %, and most preferably 52.8±3.0 wt %.

The crystal of the present invention can be confirmed to be a crystal of a nonhydrate by the fact that the water content measured by using a Karl-Fischer method described in the analysis examples later is generally 2.5 wt % or less, preferably 2.3 wt % or less, and most preferably 2.0 wt % or less.

Figure 2:
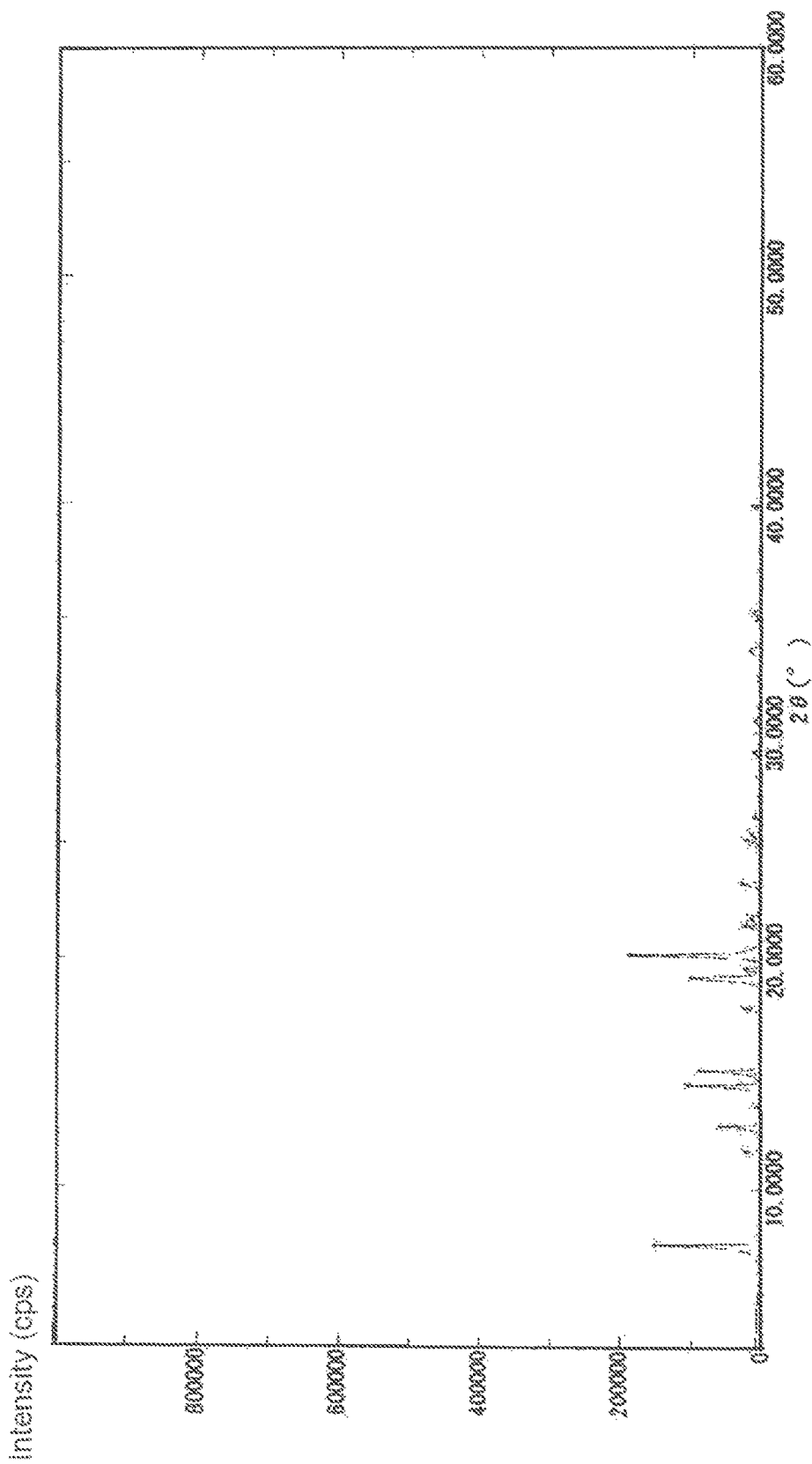
FIG. 2 illustrates the results of powder X-ray diffraction of a crystal of arginine salt nonhydrate of HMB obtained in Example 3.

The crystal of arginine salt nonhydrate of HMB includes a crystal of arginine salt nonhydrate of HMB of which powder X-ray diffraction pattern using CuKα as the X-ray source is specified by the values shown in FIGS. 1 and 2 and Tables 1 and 2. Here, FIG. 1 and FIG. 2 correspond to the diffraction results of the crystal of arginine salt nonhydrate of HMB of Table 1 and Table 2, respectively.

Figure 3:
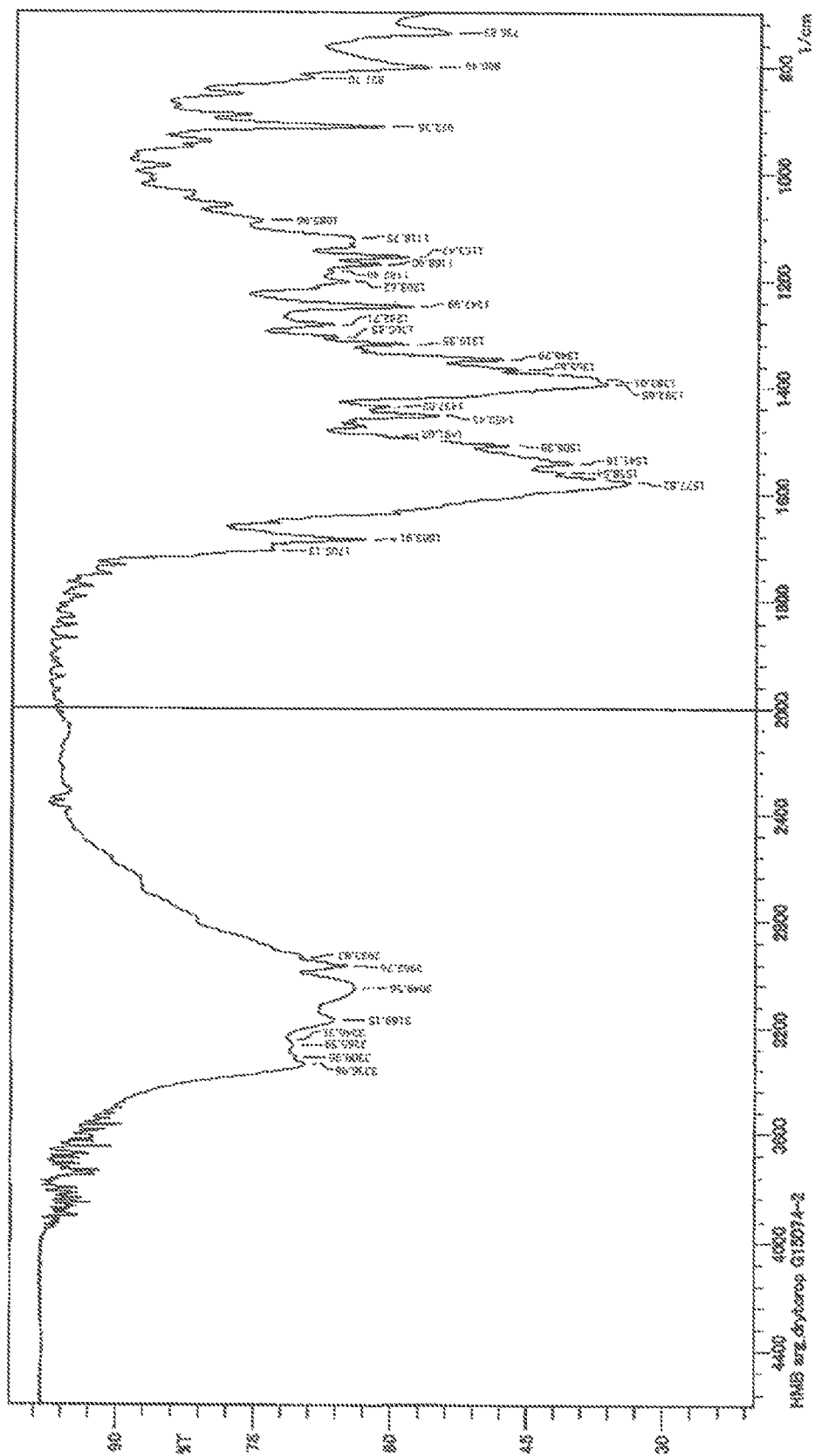
FIG. 3 illustrates the results of infrared spectroscopic (IR) analysis of the crystal of arginine salt nonhydrate of HMB obtained in Example 3.

The crystal of arginine salt nonhydrate of HMB of which the powder X-ray diffraction pattern is specified by the values shown in FIG. 2 and Table 2 includes a crystal of arginine salt nonhydrate of HMB which shows the infrared absorption spectrum illustrated in FIG. 3 when subjected to the infrared (IR) analysis described in the analysis examples later.

Specifically, as the crystal of arginine salt nonhydrate of HMB, a crystal of arginine salt nonhydrate of HMB having peaks at diffraction angles (2θ) described in the following (i) in the powder X-ray diffraction using CuKα as the X-ray source is preferable, a crystal of arginine salt nonhydrate of HMB having peaks at diffraction angles (2θ) described in the following (ii) as well as the diffraction angles (2θ) described in the following (i) is more preferable, and a crystal of arginine salt nonhydrate of HMB having peaks at diffraction angles (2θ) described in the following (iii) as well as the diffraction angles (2θ) described in the following (i) and (ii) is furthermore preferable.

(i) 7.5±0.2°, preferably 7.5±0.1°, 14.5±0.2°, preferably 14.5±010, 15.1±02°, preferably 15.1±0.1°, 19.2±0.2°, preferably 19.2±0.1°, and 20.2±0.2°, preferably 20.2±0.1°.

(ii) 11.6±0.2°, preferably 11.6±0.1°, 12.7±0.2°, preferably 12.7±0.1°, 17.9±0.2, preferably 17.9±0.1°, 21.5±0.2°, preferably 21.5±0.1°, and 23.3±0.2°, preferably 23.3±0.1°.

(iii) 19.6±0.2°, preferably 19.6±0.1°, 21.9±0.2°, preferably 21.9±0.1°, 25.2±0.2°, preferably 25.2±0.1°, 25.5±0.2°, preferably 25.5±0.1, and 33.6±0.2°, preferably 33.6±0.1°.

Figure 4:
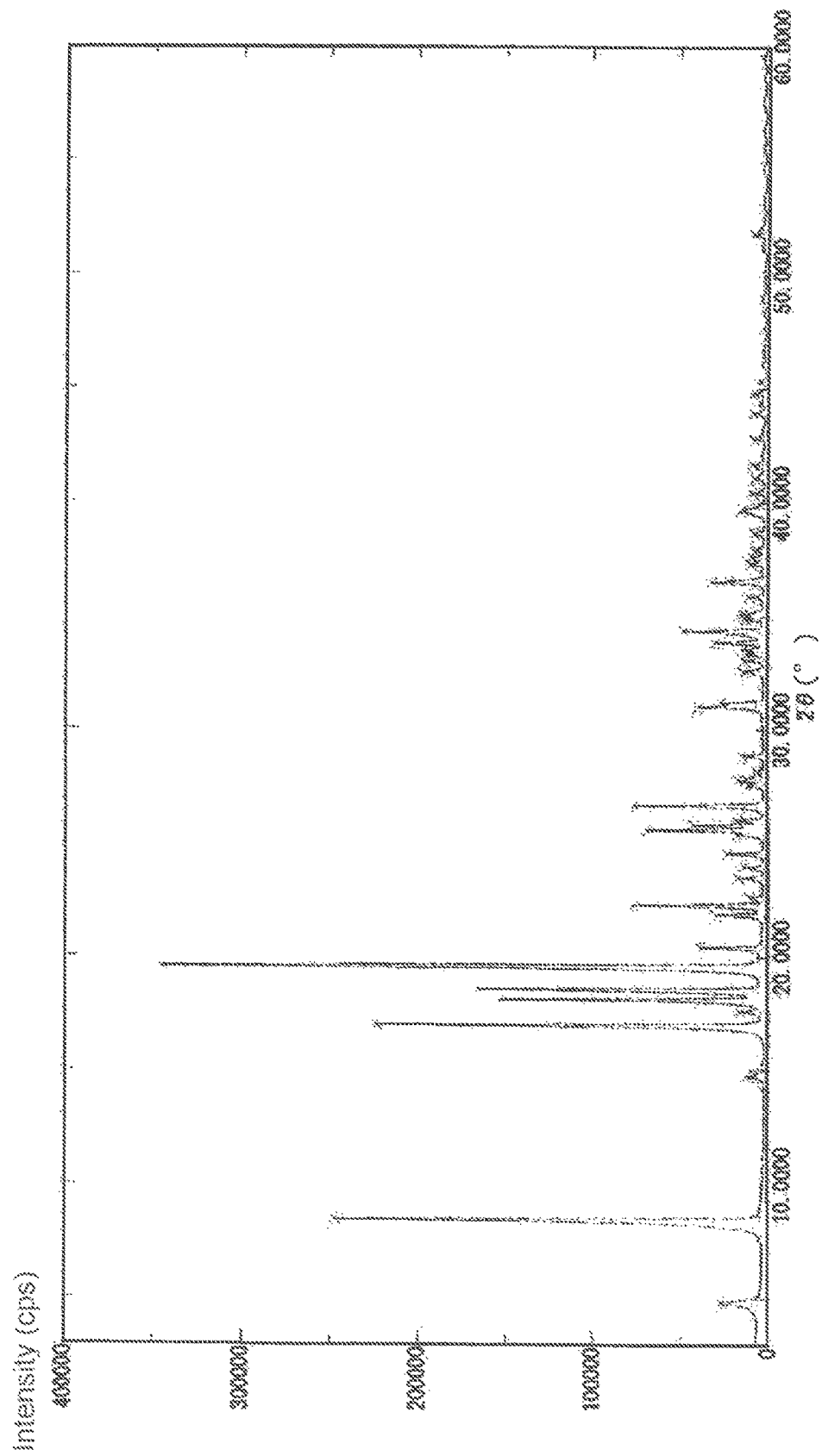
FIG. 4 illustrates the results of powder X-ray diffraction of a crystal of lysine salt nonhydrate of HMB obtained in Example 4.

The crystal of lysine salt nonhydrate of HMB includes a crystal of lysine salt nonhydrate of HMB of which powder X-ray diffraction pattern using CuKα as the X-ray source is specified by the values shown in FIG. 4 and Table 4.

Figure 5:
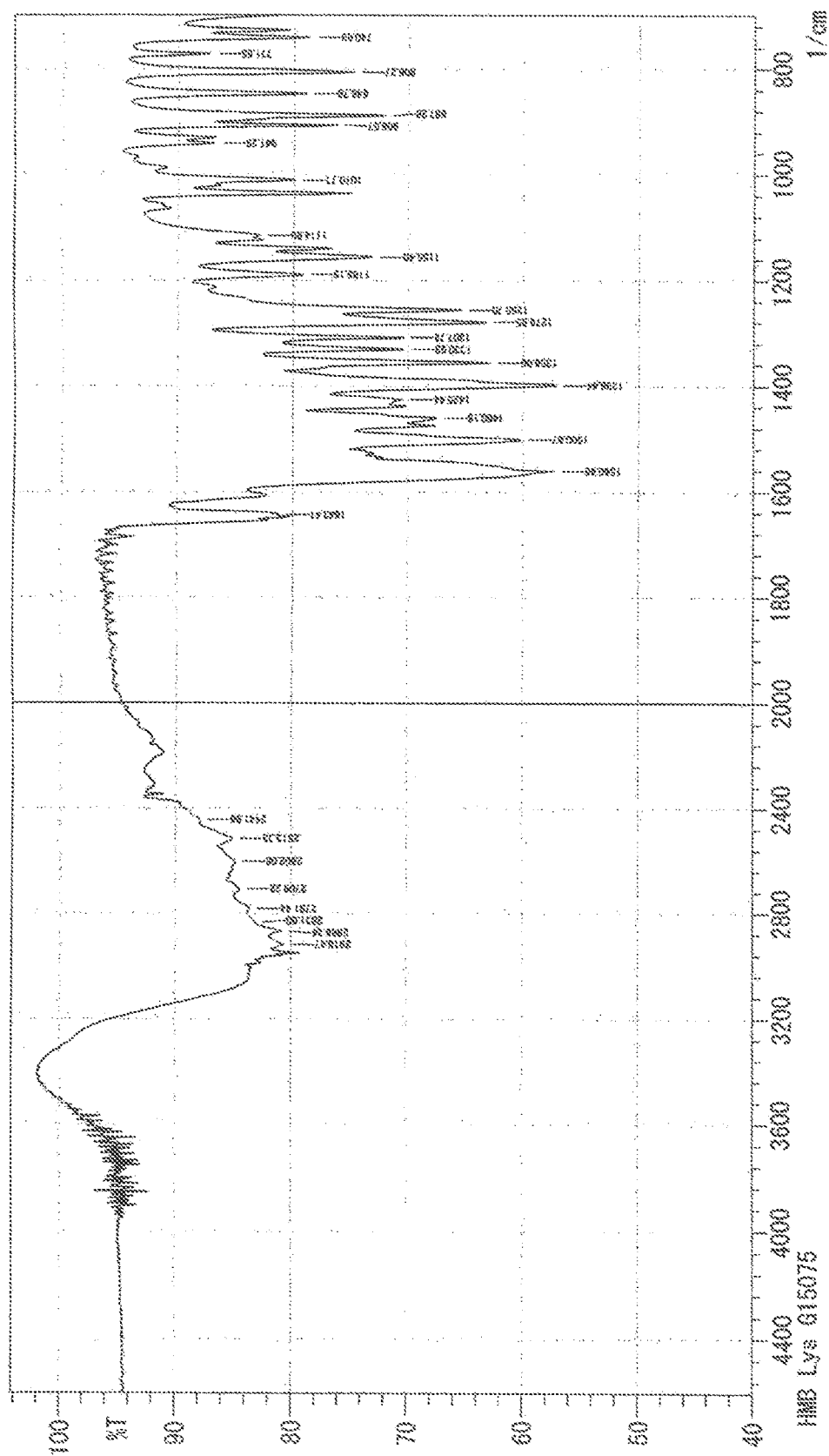
FIG. 5 illustrates the results of infrared spectroscopic (IR) analysis of the crystal of lysine salt nonhydrate of HMB obtained in Example 4.

Examples of the crystal of lysine salt nonhydrate of HMB of which the powder X-ray diffraction pattern is specified by the values shown in FIG. 4 and Table 4 include a crystal of lysine salt nonhydrate of HMB which shows the infrared absorption spectrum illustrated in FIG. 5 when subjected to the infrared spectroscopic (IR) analysis described in the analysis examples later.

Specifically, as the crystal of lysine salt nonhydrate of HMB, a crystal of lysine salt nonhydrate of HMB having peaks at diffraction angles (2θ) described in the following (i) in the powder X-ray diffraction using CuKα as the X-ray source is preferable, a crystal of lysine salt nonhydrate of HMB having peaks at diffraction angles (2θ) described in the following (ii) as well as the diffraction angles (2θ) described in the following (i) is more preferable, and a crystal of lysine salt nonhydrate of HMB having peaks at diffraction angles (2θ) described in the following (iii) as well as the diffraction angles (2θ) described in the following (i) and (ii) is furthermore preferable.

(i) 8.5±0.2°, preferably 8.5±0.1°, 17.0±0.2°, preferably 17.0±0.1°, 18.1±0.2°, preferably 18.1±0.1°, 18.5±0.2°, preferably 18.5±0.1°, and 19.5±0.2°, preferably 19.5±0.1°.

(ii) 22.2±0.2°, preferably 22.2±0.1°, 25.5±0.2°, preferably 25.5±0.1°, 25.8±0.2°, preferably 25.8±0.1°, 26.6±0.2°, preferably 26.6±0.1°, and 34.4±0.2°, preferably 34.4±0.1°.

(iii) 4.8±0.2°, preferably 4.8±0.1°, 20.4±0.2°, preferably 20.4±0.1°, 31.0±0.2°, preferably 31.0±0.1°, 33.8±0.2°, preferably 33.8±0.1°, and 36.5±0.2°, preferably 36.5±0.1°.

Figure 6:
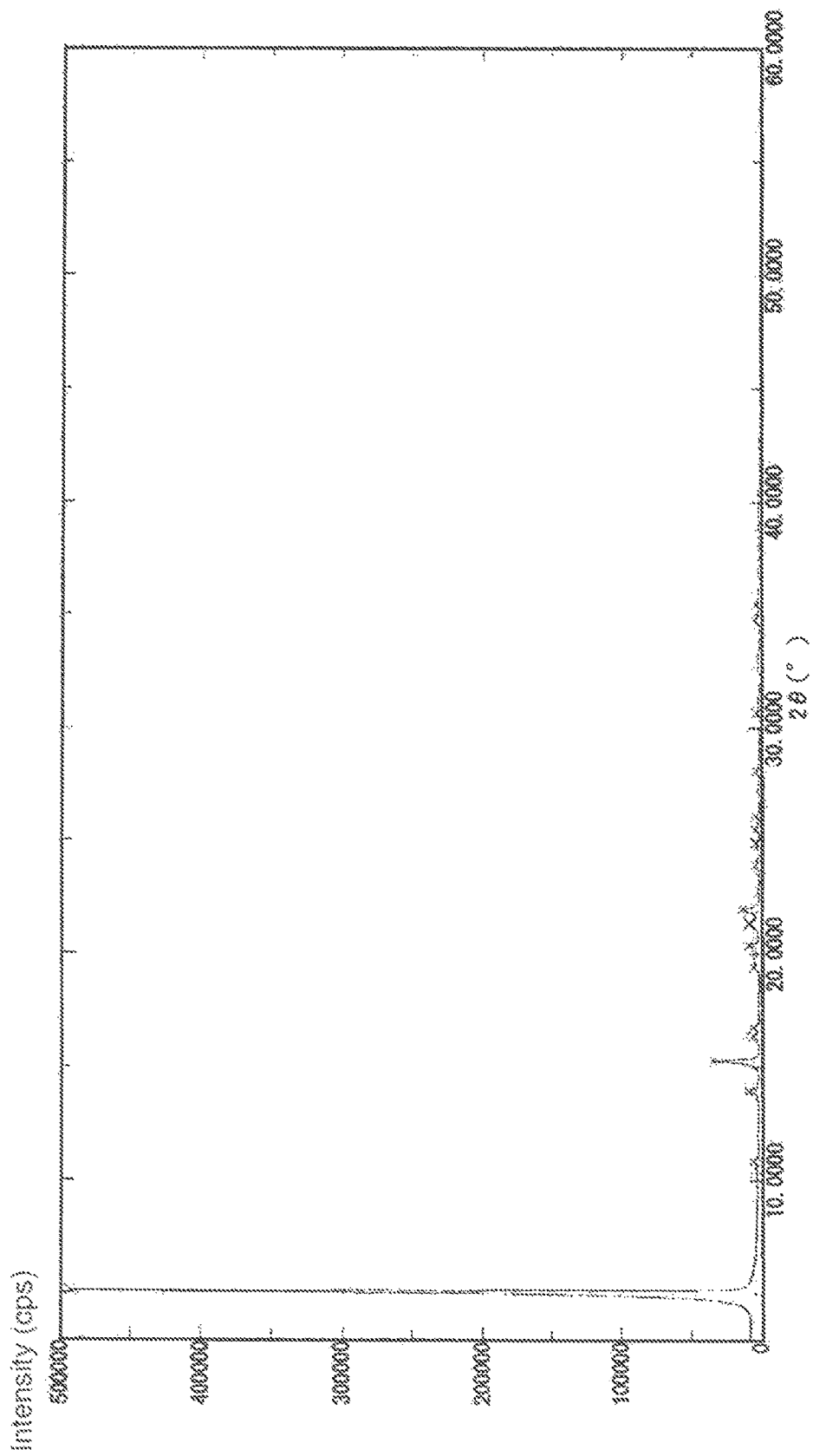
FIG. 6 illustrates the results of powder X-ray diffraction of a crystal of ornithine salt nonhydrate of HMB obtained in Example 6.
Figure 8:
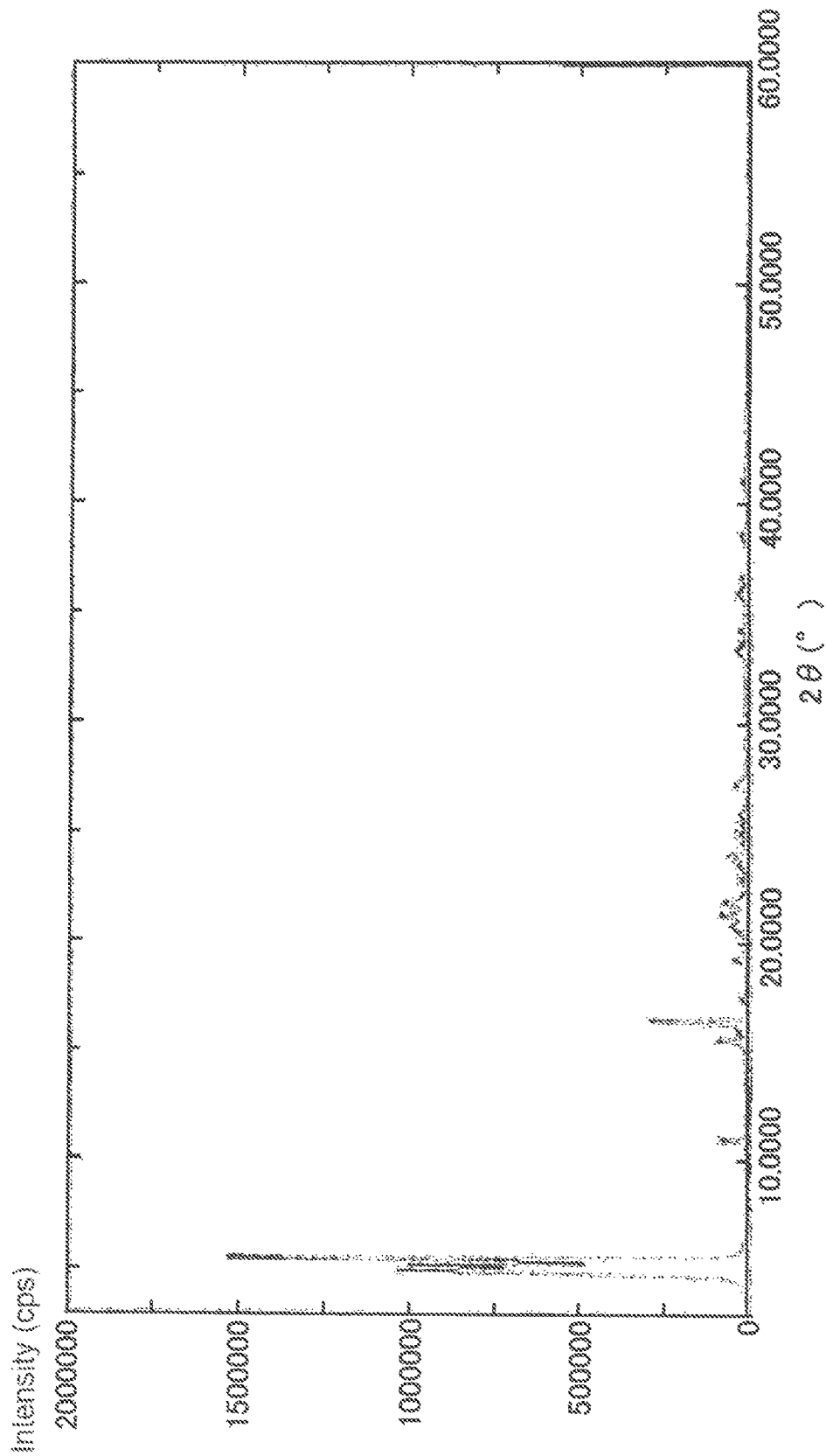
FIG. 8 illustrates the results of powder X-ray diffraction of the crystal of ornithine salt nonhydrate of HMB obtained in Example 7.

The crystal of ornithine salt nonhydrate of HMB includes a crystal of ornithine salt nonhydrate of HMB of which powder X-ray diffraction pattern using CuKα as the X-ray source is specified by the values shown in FIG. 6 and Table 6, and a crystal of ornithine salt nonhydrate of HMB of which the pattern is specified by the values shown in FIG. 8 and Table 9. Here, FIG. 6 and FIG. 8 correspond to the diffraction results of the crystal of ornithine salt nonhydrate of HMB of Table 6 and Table 9, respectively.

Figure 7:
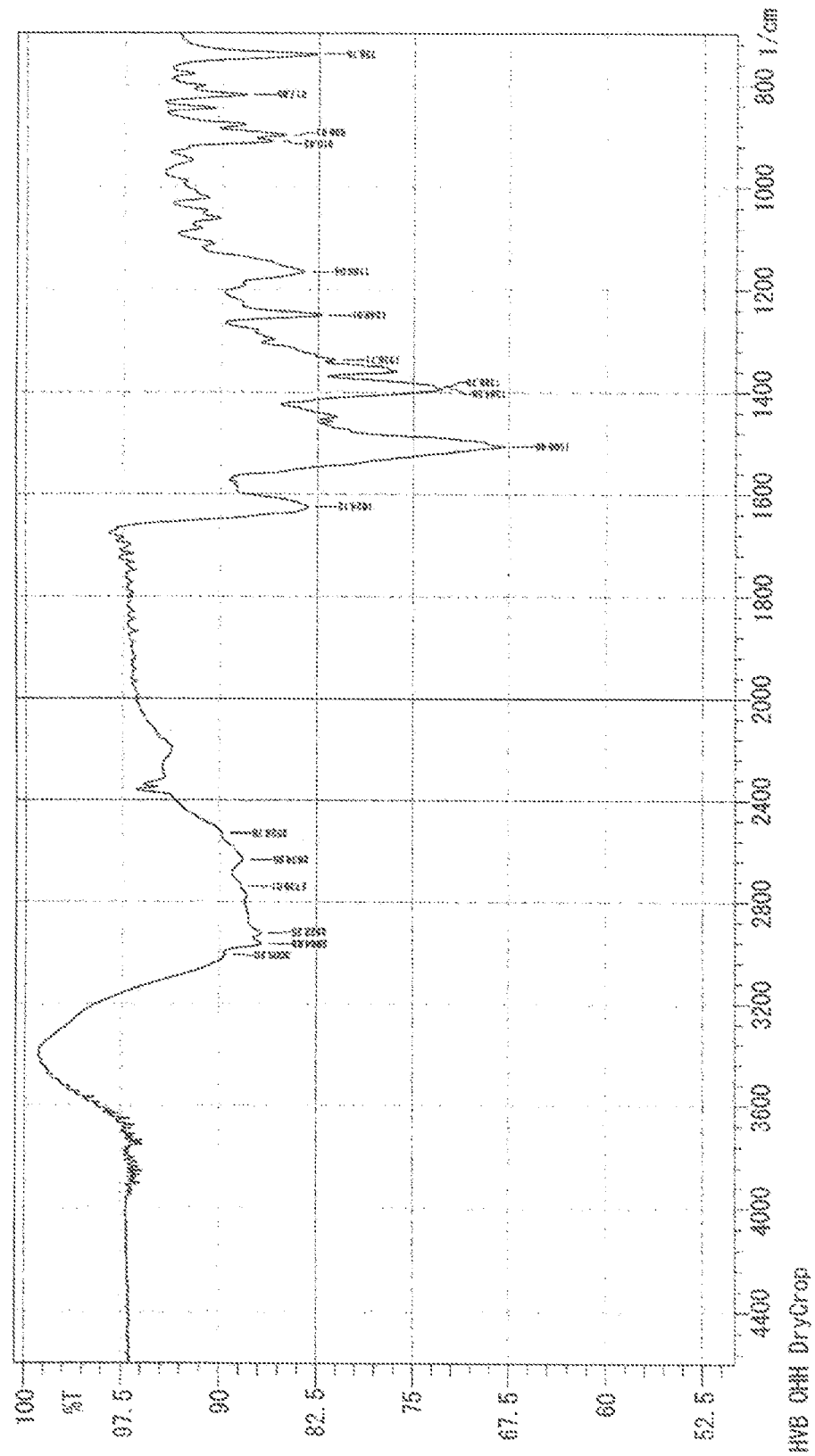
FIG. 7 illustrates the results of infrared spectroscopic (IR) analysis of the crystal of ornithine salt nonhydrate of HMB obtained in Example 6.

Examples of the crystal of ornithine salt nonhydrate of HMB of which the powder X-ray diffraction pattern is specified by the values shown in FIG. 6 and Table 6 include a crystal of ornithine salt nonhydrate of HMB which shows the infrared absorption spectrum illustrated in FIG. 7 when subjected to the infrared spectroscopic (IR) analysis described in the analysis examples later.

Specifically, as the crystal of ornithine salt nonhydrate of HMB, a crystal of ornithine salt nonhydrate of HMB having peaks at diffraction angles (2θ) described in the following (i) in the powder X-ray diffraction using CuKα as the X-ray source is preferable, a crystal of ornithine salt nonhydrate of HMB having peaks at diffraction angles (2θ) described in the following (ii) as well as the diffraction angles (2θ) described in the following (i) is more preferable, and a crystal of ornithine salt nonhydrate of HMB having peaks at diffraction angles (2θ) described in the following (iii) as well as the diffraction angles (2θ) described in the following (i) and (ii) is furthermore preferable.

(i) 5.1±0.2°, preferably 5.1±0.1°, 14.0±0.2°, preferably 14.0±0.1°, 15.3±0.2°, preferably 15.3±0.1°, 20.4±0.2°, preferably 20.4±0.1°, and 21.9±0.2°, preferably 21.9±0.1°.

(ii) 16.4±0.2°, preferably 16.4±0.1°, 16.8±0.2°, preferably 16.8±0.1°, 19.4±0.2°, preferably 19.4±0.1°, 21.4±0.2°, preferably 21.4±0.1°, and 25.5±0.2°, preferably 25.5±0.1°.

(iii) 0.9±0.2°, preferably 0.9±0.1°.

Furthermore, as the crystal of ornithine salt nonhydrate of HMB, a crystal of ornithine salt nonhydrate of HMB having peaks at diffraction angles (2θ) described in the following (i) in the powder X-ray diffraction using CuKα as the X-ray source is preferable, a crystal of ornithine salt nonhydrate of HMB having peaks at diffraction angles (2θ) described in the following (ii) as well as the diffraction angles (2θ) described in the following (i) is more preferable, and a crystal of ornithine salt nonhydrate of HMB having peaks at diffraction angles (2θ) described in the following (iii) as well as the diffraction angles (2θ) described in the following (i) and (ii) is furthermore preferable.

(i) 4.9±0.2°, preferably 4.9±0.1°, 5.2±02°, preferably 5.2±0.1°, 5.5±0.2°, preferably 5.5±0.1°, 10.9±0.2°, preferably 10.9±0.1°, and 15.5±0.2°, preferably 15.5±0.1°.

(ii) 15.9±0.2°, preferably 15.9±0.1°, 16.4±0.2°, preferably 16.4±0.1°, 17.4±0.2°, preferably 17.4±0.1°, 19.2±0.2° preferably 19.2±0.1°, and 20.4±0.2°, preferably 20.4±0.1°.

(iii) 20.8±0.2°, preferably 20.8±0.1°, 21.3±0.2°, preferably 21.3±0.1°, 21.8±0.2°, preferably 21.8±0.1°, 22.2±0.2° preferably 22.2±0.1°, and 22.8±0.2°, preferably 22.8±0.1°.

2. Method for Producing Crystal of Present Invention

A method for producing the crystal of the present invention is a production method described in the following (1) or (2) (hereinafter will be referred to as "the method for producing the crystal" in some cases).

(1) Method 1 for Producing Crystal of Present Invention

Examples of the method for producing the crystal of the present invention include a method for producing a crystal of an amino acid salt of HMB, including a step of dissolving an amorphous of amino acid salt of HMB in a solvent containing alcohol, a step of precipitating a crystal of an amino acid salt of HMB by stirring or allowing the solvent to left stand, and a step of collecting a crystal of an amino acid salt of HMB from the solvent.

Examples of the amino acid preferably include a basic amino acid, more preferably arginine, ornithine, lysine, and histidine, furthermore preferably arginine, ornithine, and lysine, and most preferably arginine. As an amino acid, any one of the L form and the D form may be used, but the L form is preferable.

Examples of the alcohol preferably include at least one alcohol selected from the group consisting of C1 to C6 alcohols, more preferably at least one alcohol selected from the group consisting of C1 to C3 alcohols, furthermore preferably at least one alcohol selected from the group consisting of methanol, ethanol, n-propanol, and isopropyl alcohol, and still furthermore preferably at least one alcohol selected from the group consisting of methanol and ethanol, and most preferably ethanol.

The alcohol can be used by mixing one or more kinds thereof. In addition, water may be contained in the solvent containing alcohol. The water content in the solvent containing alcohol can generally be 40 wt % or less, preferably 20 wt % or less, furthermore preferably 10 wt % or less, and most preferably 5 wt % or less.

Examples of a method of dissolving an amorphous of amino acid salt of HMB in the solvent containing alcohol include a method in which an amorphous of amino acid salt of HMB is suspended in the solvent and then heated to obtain a solution, or a method in which the solvent is filtrated to obtain a filtrate.

The examples of a heating temperature in the method in which an amorphous of amino acid salt of HMB is suspended in the solvent, and then heated to obtain a solution include generally 0° C. to 80° C., preferably 20° C. to 70° C., and most preferably 40° C. to 60° C. The examples of heating time can generally include 10 minutes to 6 hours, preferably 20 minutes to 4 hours, and most preferably 30 minutes to 2 hours.

The amorphous of amino acid salt of HMB can be obtained by a method in Example 1 described below. The solvent obtained by dissolving the amorphous of amino acid salt of HMB therein is stirred or left to stand, and thereby a crystal of an amino acid salt of HMB can be precipitated.

Examples of a concentration of the amorphous of amino acid salt of HMB to be dissolved in the solvent containing alcohol preferably include 50 g/L or more, more preferably 100 g/L or more, and furthermore preferably 150 g/L or more.

A crystal of an amino acid salt of HMB may be precipitated by adding a crystal of an amino acid salt of HMB as a seed crystal to the solvent containing alcohol in which the amorphous of amino acid salt of HMB is dissolved, and then stirring or allowing the solvent to left stand. The addition of the seed crystal to the solvent can accelerate a precipitation rate. The seed crystal in the solvent is added to become a concentration of generally 0.05 to 15 wt %, preferably 0.5 to 10 wt %, and most preferably 2 to 7 wt %.

The crystal of an amino acid salt of HMB can be obtained by a method in Examples 2, 4, or 5 described below.

Examples of a temperature for stirring or allowing the solvent to left stand include generally 0° C. to 80° C., preferably 5° C. to 50° C., and most preferably 10° C. to 30° C. Examples of time for stirring or allowing the solvent to left stand include generally 1 to 100 hours, preferably 3 to 48 hours, and most preferably 5 to 24 hours.

Examples of a method for collecting a crystal of an amino acid salt of HMB from the solvent are not particularly limited, but include filtration, pressurized filtration, suction filtration, centrifugal separation, and the like. Furthermore, in order to reduce attachment of the mother liquid and enhance the crystal quality, the crystal can be appropriately washed.

The solution used for washing the crystal is not particularly limited, but a solution in which one or a plurality of kinds selected from water, methanol, ethanol, acetone, n-propanol, and isopropyl alcohol are mixed in an arbitrary ratio, can be used.

The crystal of an amino acid salt of HMB can be obtained by drying the wet crystal obtained as above. As for the drying condition, any method may be used as long as the form of the crystal of an amino acid salt of HMB can be maintained, and reduced-pressure drying, vacuum drying, fluidized-bed drying, forced air drying, or the like can be applied. The drying temperature may be any temperature as long as the attached water or solvent can be removed, but the temperature is preferably 80° C. or less, more preferably 60° C. or less.

Under the above-described crystallization conditions, a high-purity crystal of an amino acid salt of HMB can be obtained. The purity of the crystal is generally 95% or more, preferably 96% or more, more preferably 97% or more, and most preferably 97.5% or more.

The crystal of an amino acid salt of HMB, which can be produced by the above-described production method, includes a crystal of arginine salt nonhydrate of HMB of which powder X-ray diffraction pattern using CuKα as the X-ray source is specified by the values shown in FIGS. 1 and 2 and Tables 1 and 2.

(2) Method 2 for Producing Crystal of Present Invention

Examples a method for producing the crystal of the present invention include a method for producing a crystal of an amino acid salt of HMB, which includes a step of concentrating an aqueous HMB solution containing an amino acid-containing compound and having a pH of 2.5 to 11.0 and thereby precipitating a crystal of an amino acid salt of HMB in the aqueous solution, and a step of collecting the crystal of an amino acid salt of HMB from the aqueous solution.

HMB contained in the aqueous HMB solution may be a compound produced by any production method such as fermentation method, enzyme method, extraction method from natural products, or chemical synthesis method.

In the case where a solid matter hindering the crystallization is contained in the aqueous HMB solution, the solid matter can be removed using centrifugal separation, filtration, ceramic filter, or the like. In the case where a water-soluble impurity or salt hindering the crystallization is contained in the aqueous HMB solution, the water-soluble impurity or salt can be removed, for example, by passing the solution through a column filled with an ion exchange resin, or the like.

In the case where a hydrophobic impurity hindering the crystallization is contained in the aqueous HMB solution, the hydrophobic impurity can be removed, for example, by passing the solution through a column filled with a synthetic adsorption resin, activated carbon, or the like. It is possible to prepare the aqueous solution to have an HMB concentration of usually 500 g/L or more, preferably 600 g/L or more, more preferably 700 g/L or more, and most preferably 800 g/L or more.

Examples of the amino acid-containing compound preferably include a basic amino acid-containing compound, more preferably an arginine-containing compound, a lysine-containing compound, an ornithine-containing compound, and a histidine-containing compound, and most preferably an arginine-containing compound, a lysine-containing compound, and an ornithine-containing compound. As an amino acid in the amino acid-containing compound, any one of the L form and the D form can be used, but the L form is preferable.

Examples of the arginine-containing compound include free arginine and arginine hydrochloride. In a case of using free arginine as the arginine-containing compound, it is possible to obtain an aqueous HMB solution containing the arginine-containing compound having a pH of generally 2.5 to 11.0, preferably 2.8 to 10.5, and most preferably 3.0 to 10.0 by adjusting a pH of the aqueous HMB solution by using arginine.

Examples of the lysine-containing compound include free lysine and lysine hydrochloride. In a case of using free lysine as the lysine-containing compound, it is possible to obtain an aqueous HMB solution containing the lysine-containing compound having a pH of generally 2.5 to 11.0, preferably 2.8 to 10.5, and most preferably 3.0 to 10.0 by adjusting a pH of the aqueous HMB solution by using lysine.

Examples of the ornithine-containing compound include free ornithine and ornithine hydrochloride. In a case of using free ornithine as the ornithine-containing compound, it is possible to obtain an aqueous HMB solution containing the ornithine-containing compound having a pH of generally 2.5 to 11.0, preferably 2.8 to 10.5, and most preferably 3.0 to 10.0 by adjusting a pH of the aqueous HMB solution by using ornithine.

Examples of a method for concentrating the aqueous HMB solution and thereby precipitating a crystal of an amino acid salt of HMB in the aqueous solution include a method for concentrating the aqueous solution under reduced pressure.

In the method for concentrating the aqueous HMB solution under reduced pressure, the temperature of the aqueous solution is generally from 0° C. to 100° C., preferably from 10° C. to 90° C., most preferably from 20° C. to 60° C. In the method for concentrating the aqueous solution under reduced pressure, the pressure reduction time is generally from 1 to 120 hours, preferably from 2 to 60 hours, most preferably from 3 to 50 hours.

In the step of precipitating the crystal of an amino acid salt of HMB in the aqueous solution, a crystal of an amino acid salt of HMB may be added to the aqueous HMB solution as a seed crystal. The seed crystal is added to the aqueous solution such that the concentration thereof becomes generally 0.05 to 15 wt %, preferably 0.5 to 10 wt %, and most preferably 2 to 7 wt %. Specifically, the crystal of an amino acid salt of HMB can be obtained by, for example, a method in Examples 2, 4, or 5 described below.

In the step of precipitating a crystal of an amino acid salt of HMB in the aqueous solution, the crystal of an amino acid salt of HMB may be precipitated by adding or adding dropwise, in the aqueous HMB solution, at least one solvent selected from the group consisting of alcohol, nitrile, and ketone. Alcohol, nitrile, and ketone may be used alone, or a plurality of kinds thereof may be used in combination.

When adding or adding dropwise the solvent, the seed crystal may be added before precipitation of the crystal of an amino acid salt of HMB. The timing of adding the seed crystal can be generally within 0 to 5 hours, preferably within 0 to 4 hours, and most preferably within 0 to 3 hours, after starting adding dropwise or adding the solvent. Furthermore, the seed crystal may be added before adding or adding dropwise the solvent in the aqueous HMB solution.

Examples of the alcohol include the examples same as those described in 2. (1). Examples of the nitrile are preferably acetonitrile. Examples of the ketone are preferably at least one ketone selected from the group consisting of acetone, methyl ethyl ketone, methyl isobutyl ketone and diethyl ketone, more preferably at least one ketone selected from the group consisting of acetone and methyl ethyl ketone, and most preferably acetone.

When adding or adding dropwise the solvent in the aqueous HMB solution, the temperature of the aqueous solution may be any temperature as long as it is a temperature not causing degradation of HMB, but in order to enhance the crystallization ratio of a crystal of amino acid salt nonhydrate of HMB by lowering the solubility, the temperature is generally 80° C. or less, preferably 70° C. or less, more preferably 60° C. or less, and most preferably 50° C. or less. A lower limit value of the temperature is generally 0° C. or more, and preferably 10° C. or more.

The amount in which the solvent is added or added dropwise to the aqueous HMB solution is generally from 0.5 to 30 times, preferably from 0.5 to 25 times, and most preferably from 0.5 to 10 times the amount of the aqueous solution.

The time for which the solvent is added or added dropwise to the aqueous HMB solution is generally from 30 minutes to 48 hours, preferably from 2 to 30 hours, and most preferably from 3 to 20 hours.

After a crystal of an amino acid salt of HMB is precipitated as described above, the precipitated crystal may be further ripened generally for 1 to 48 hours, preferably for 1 to 24 hours, and most preferably for 1 to 12 hours. The term "be ripened" means to grow the crystal by once stopping the step of precipitating a crystal of amino acid salt nonhydrate of HMB. After ripening the crystal, the step of precipitating a crystal of an amino acid salt of HMB may be restarted.

The method for collecting a crystal of an amino acid salt of HMB is not particularly limited and examples thereof include collection by filtration, pressurized filtration, suction filtration, centrifugal separation, and the like. Furthermore, in order to reduce adhesion of the mother liquid and enhance the crystal quality, the crystal can be appropriately washed.

A solution used for washing the crystal is not particularly limited and it is possible to use a solution in which one or a plurality of kinds thereof selected from water, methanol, ethanol, acetone, n-propanol, isopropyl alcohol, acetonitrile, acetone, methyl ethyl ketone, methyl isobutyl ketone, and diethyl ketone, are mixed in an arbitrary ratio.

The thus-obtained wet crystal is dried, whereby a crystal of an amino acid salt of HMB of the present invention can be obtained. As for the drying condition, reduced-pressure drying, vacuum drying, fluidized-bed drying, or forced air drying may be applied. The drying temperature may be any temperature as long as the attached water or solvent can be removed, but the temperature is preferably 80° C. or less, and more preferably 60° C. or less.

Under the above-described crystallization conditions, a high-purity crystal of an amino acid salt of HMB can be obtained. The purity of the crystal of an amino acid salt of HMB is generally 93% or more, preferably 94% or more, more preferably 95% or more, and most preferably 96% or more.

Examples of the crystal of an amino acid salt of HMB produced by the above production method include a crystal of lysine salt nonhydrate of HMB of which powder X-ray diffraction pattern using CuKα as the X-ray source is specified by the values shown in FIG. 4 and Table 4, a crystal of ornithine salt nonhydrate of HMB of which the pattern is specified by the values shown in FIG. 6 and Table 6, and a crystal of ornithine salt nonhydrate of HMB of which the pattern is specified by the values shown in FIG. 8 and Table 9.

Analysis Examples (1) Powder X-Ray Diffraction

A powder X-ray diffraction apparatus (XRD), Ultima IV (manufactured by Rigaku Corporation), was used, and the measurement was performed according to the instruction book.

(2) Measurement of Concentration and Purity

The concentration of HMB and purity of various salts were measured using the following HPLC analysis conditions.

Guard column: Shodex SUGAR SH-G φ6.0×50 mm
Column: SUGAR SH1011 φ8.0×300 mm×2 columns in series
Column temperature: 60° C.
Buffer: 0.005 mol/L of an aqueous sulfuric acid solution
Flow velocity: 0.6 mL/min
Detector: UV detector (wavelength: 210 nm)

(3) Measurement of Water Content of Crystal by Karl-Fischer Method

An automatic water measurement apparatus, AQV-2200 (manufactured by Hiranuma Sangyo Co., Ltd.), was used, and the water content of the crystal was measured according to the instruction book.

(4) Measurement of Amino Acid Content in Crystal

The amino acid content was measured by a phthalaldehyde (OPA) method by using HPLC having a fluorescence detector.

(5) Measurement of Melting Point

Melting Point M-565 (manufactured by BÜCHI Labortechnik AG) was used, and the melting point was measured using the following conditions according to the instruction book. 100° C. to 250° C., 2° C./min (6) Infrared Spectroscopic (IR) Analysis Model FTIR-8400 (manufactured by Shimadzu Corporation) was used, and the analysis was performed according to the instruction book.

Reference Example 1

Manufacturing of Free HMB Solution

Reagent of HMB calcium salt of 76.5 g in terms of the free form was dissolved in 850 mL of water. The aqueous solution passed through 640 mL of strong cation exchange resin, XUS-40232.01(H$^+$) (manufactured by The DOW Chemical Company) to remove Ca, and therefore 1.25 L of a solution containing 76.4 g of the free HMB was obtained.

REFERENCE EXAMPLE 2

Examination on Crystallization of Arginine salt of HMB

Crystallization of arginine salt of HMB was examined with reference to U.S. Patent Application Publication No. 2004/0176449. 48 mL of the aqueous solution containing 2.31 g of the free HMB was obtained in the same manner as in Reference Example 1. The obtained aqueous solution was concentrated to become 12 mL, and then 24 mL of isobutanol was added thereto. Furthermore, when free arginine of 2.41 g was added and stirred for 1 hour at room temperature, a white transparent solution having two phases was obtained. When only an aqueous phase was collected and the aqueous phase was concentrated for 20 hours under conditions of 50° C. and 15 mbar, a white precipitate of 6.5 g was obtained. When the powder was observed by using a polarizing microscope, it was confirmed that the powder is a formless candy-like solid showing no polarization, and therefore is found to be noncrystalline and amorphous (melting point: 98° C. to 126° C., 10° C./min). As above, the crystal of arginine salt of HMB was not obtained by the method described in U.S. Patent Application Publication No. 2004/0176449.

Examination on Crystallization of Arginine Salt of HMB

Crystallization of arginine salt of HMB was examined with reference to U.S. Patent Application No. 2004/0176449. 48 mL of the aqueous solution containing 2.31 g of the free HMB was obtained in the same manner as in Reference Example 1. The obtained aqueous solution was concentrated to become 12 mL, and then 24 mL of isobutanol was added thereto. Furthermore, when free arginine of 2.41 g was added and stirred for 1 hour at room temperature, a white transparent solution having two phases was obtained. When only an aqueous phase was collected and the aqueous phase was concentrated for 20 hours under conditions of 50° C. and 15 mbar, a white precipitate of 6.5 g was obtained. When the powder was observed by using a polarizing microscope, it was confirmed that the powder is a formless candy-like solid showing no polarization, and therefore is found to be noncrystalline and amorphous (melting point: 98° C. to 126° C., 10° C./min). As above, the crystal of arginine salt of HMB was obtained by the method described in U.S. Patent Application No. 2004/0176449.

EXAMPLES

Examples are described below, but the present invention is not limited to the following Examples.

Example 1

Acquisition of Noncrystalline and Amorphous Arginine Salt of HMB

To 200 mL of the aqueous free HMB solution obtained in Reference Example 1, 160 mL of an aqueous 128 g/L L-arginine solution was added to adjust the pH to 7.05. The obtained aqueous solution was provided for the next step.

360 mL of the aqueous solution was concentrated at 50° C. under reduced pressure at 15 mbar to remove the solvent, and thereby 31.1 g of white powder was obtained. From the fact that no polarization was shown when the powder was observed by using a polarizing microscope, it was found that the powder is noncrystalline and amorphous.

Example 2

Acquisition of Seed Crystal of Arginine Salt Nonhydrate of HMB 1.5 mL of 100%-EtOH was added to 150 mg of the noncrystalline and amorphous arginine salt of HMB obtained in Reference Example 1 and heated at 50° C. to be completed dissolved.

A crystal was caused to naturally develop by stirring the aqueous solution at 25° C. for 12 hours. The crystal slurry was further ripened for 12 hours, and the crystal was then collected by filtration, and forced air-dried at 25° C. for 12 hours to obtain 60 mg of a crystal.

The results of powder X-ray diffraction of the crystal are shown in FIG. 1 and Table 1. In the Table, "2θ" indicates a diffraction angle (2θ°), and "Relative Intensity" indicates a relative intensity ratio ($I/I_0$). The relative intensity ratio is shown when the ratio is 1 or more.

TABLE 1

| 2θ | Relative Intensity |
|---|---|
| 7.5 | 100 |
| 11.6 | 4 |
| 12.7 | 8 |
| 14.5 | 14 |
| 15.1 | 69 |
| 17.9 | 4 |
| 19.2 | 11 |
| 19.6 | 4 |
| 20.2 | 25 |
| 21.5 | 4 |
| 21.8 | 2 |
| 22.7 | 4 |
| 23.3 | 5 |
| 25.2 | 3 |
| 25.5 | 2 |
| 29.1 | 2 |
| 30.4 | 3 |
| 33.6 | 2 |
| 35.3 | 2 |
| 39.9 | 1 |

Example 31

Acquisition of Crystal of Arginine Salt Nonhydrate of HMB 160 mL of 100%-EtOH was added to 27.8 g of the noncrystalline and amorphous arginine salt of HMB obtained in Reference Example 1 and heated at 50° C. to be completely dissolved.

A crystal was caused to naturally develop by adding 0.1 g of the seed crystal of arginine salt of HMB obtained according to Example 2 to the aqueous solution. The crystal slurry was stirred at 25° C. for 12 hours, ripened, and the crystal was then collected by filtration, and forced air-dried at 25° C. to obtain 23.6 g of a crystal.

11.6 g of the obtained crystal was further dried at 40° C. for 24 hours under reduced pressure (at 15 mbar), and therefore 9.0 g of a crystal was obtained. It was possible to acquire 97.8% (area %) or more of the crystal of arginine salt nonhydrate of HMB in the measurement of the purity using HPLC.

The results of powder X-ray diffraction of the crystal are shown in FIG. 2 and Table 2. The results of infrared spectroscopic (IR) analysis are shown in FIG. 3. In the Table, "2θ" indicates a diffraction angle (2θ0), and "Relative Intensity" indicates a relative intensity ratio ($I/I_0$). The relative intensity ratio is shown when the ratio is 5 or more.

TABLE 2

| 2θ | Relative Intensity |
|---|---|
| 7.5 | 81 |
| 11.6 | 14 |
| 12.7 | 33 |
| 13.5 | 5 |
| 14.5 | 57 |
| 15.1 | 49 |
| 17.9 | 15 |
| 19.2 | 55 |
| 19.6 | 14 |
| 20.2 | 100 |
| 21.5 | 15 |
| 21.9 | 10 |
| 23.3 | 17 |
| 25.2 | 13 |

TABLE 2-continued

| 2θ | Relative Intensity |
|---|---|
| 25.5 | 9 |
| 26.3 | 7 |
| 29.1 | 6 |
| 30.5 | 6 |
| 33.6 | 10 |
| 35.3 | 7 |
| 39.9 | 6 |

As a result of measuring the L-arginine content in the crystal by HPLC, the content was 61.7 wt %, which substantially coincided with the theoretical value (59.6 wt %) of a mono-arginine salt. In addition, as a result of measuring the water amount contained in the crystal by the Karl-Fischer method, the content was 0.5 wt %.

Accordingly, it was found that the crystal is a crystal of arginine salt nonhydrate of HMB. Various physical properties of the crystal acquired in Example 3 are shown in Table 3.

TABLE 3

| Water % | Arginine content % | Melting point ° C. |
|---|---|---|
| 0.5 | 61.7 | 177.9 |

Example 4

Acquisition of Crystal of Lysine Salt Nonhydrate of HMB

To 200 mL of the aqueous free HMB solution obtained in Reference Example 1, 94 mL of an aqueous 200 g/L L-lysine solution was added to adjust the pH to 6.03. The obtained aqueous solution was provided for the next step. When the aqueous solution was concentrated under conditions of 50° C. and 15 mbar such that the weight of the concentrated solution becomes 33.4 g, a crystal was caused to develop naturally, and therefore white slurry was obtained. 20 mL of acetonitrile was added to the slurry, stirred at 50° C. for 1 hour, ripened, and the crystal was then collected by filtration.

The obtained crystal was washed with 20 mL of acetonitrile, and then dried at 40° C. for 24 hours under reduced pressure (at 15 mbar), and therefore 5.0 g of a crystal was obtained. It was possible to acquire 97.4% (area %) or more of the crystal of lysine salt nonhydrate of HMB in the measurement of the purity using HPLC.

The results of powder X-ray diffraction of the crystal are shown in FIG. 4 and Table 4. The results of infrared spectroscopic (IR) analysis are shown in FIG. 5. In the Table, "2θ" indicates a diffraction angle (2θ°), and "Relative Intensity" indicates a relative intensity ratio ($I/I_0$). The relative intensity ratio is shown when the ratio is 2 or more.

TABLE 4

| 2θ | Relative Intensity |
|---|---|
| 4.8 | 9 |
| 8.5 | 72 |
| 14.7 | 5 |
| 14.8 | 3 |
| 17.0 | 65 |
| 17.6 | 5 |
| 18.1 | 45 |
| 18.5 | 48 |
| 19.5 | 100 |

TABLE 4-continued

| 2θ | Relative Intensity |
|---|---|
| 20.4 | 12 |
| 21.8 | 9 |
| 22.2 | 23 |
| 22.6 | 4 |
| 23.4 | 6 |
| 23.9 | 5 |
| 24.5 | 7 |
| 25.3 | 6 |
| 25.5 | 21 |
| 25.8 | 13 |
| 26.0 | 6 |
| 26.6 | 23 |
| 27.5 | 4 |
| 27.8 | 6 |
| 27.8 | 5 |
| 28.2 | 2 |
| 28.9 | 5 |
| 31.0 | 12 |
| 31.2 | 8 |
| 32.5 | 5 |
| 33.0 | 5 |
| 33.3 | 4 |
| 33.5 | 5 |
| 33.8 | 10 |
| 34.4 | 14 |
| 34.9 | 5 |
| 35.0 | 4 |
| 35.1 | 5 |
| 35.8 | 4 |
| 36.5 | 10 |
| 36.6 | 7 |
| 37.3 | 4 |
| 37.6 | 3 |
| 37.9 | 3 |
| 38.7 | 3 |
| 39.6 | 5 |
| 39.7 | 5 |
| 40.5 | 3 |
| 41.1 | 3 |
| 41.7 | 3 |
| 42.8 | 3 |
| 43.9 | 3 |
| 44.8 | 3 |
| 51.8 | 3 |

As a result of measuring the L-lysine content in the crystal by HPLC, the content was 54.8 wt %, which substantially coincided with the theoretical value (55.3 wt %) of a monolysine salt. In addition, as a result of measuring the water amount contained in the crystal by the Karl-Fischer method, the content was 0.1 wt %.

Accordingly, it was found that the crystal is a crystal of lysine salt nonhydrate of HMB. Various physical properties of the crystal acquired in Example 4 are shown in Table 5.

TABLE 5

| Water % | Lysine content % | Melting point ° C. |
|---|---|---|
| 0.1 | 54.8 | 186.2 |

Example 5

Acquisition of Seed Crystal of Ornithine Salt Nonhydrate of HMB

To 20 mL of the aqueous free HMB solution obtained in Reference Example 1, an aqueous 510 g/L L-ornithine solution was added to adjust the pH to 7.80. The obtained aqueous solution was provided for the next step. When the aqueous solution was concentrated under conditions of 50° C. and 15 mbar, 2.8 g of a white precipitate was obtained. From the fact that no polarization was shown when the powder was observed by using a polarizing microscope, it was found that the powder is a crystal.

Example 6

Acquisition 1 of Crystal of Ornithine Salt Nonhydrate of HMB

To 20 mL of the aqueous free HMB solution obtained in Reference Example 1, 2.1 mL of an aqueous 510 g/L L-ornithine solution was added to adjust the pH to 7.08. The obtained aqueous solution was provided for the next step. After the aqueous solution was concentrated under conditions of 50° C. and 15 mbar such that the weight of the concentrated solution becomes 3.9 g, and then 0.1 g of the seed crystal of ornithine salt nonhydrate of HMB obtained according to Example 5 was added thereto, 9 mL of 100%-ethanol was added dropwise over 30 minutes, and therefore the crystal was precipitated.

The crystal slurry was ripened for 12 hours and the crystal was then collected by filtration, washed with an aqueous 100%-ethanol solution, forced air-dried at 25° C., and further dried for 24 hours at room temperature under reduced pressure (at 15 mbar), and therefore 250 mg of a crystal was obtained.

It was possible to acquire 96.3% (area %) or more of the crystal of ornithine salt nonhydrate of HMB in the measurement of the purity using HPLC. The results of powder X-ray diffraction of the crystal are shown in FIG. 6 and Table 6. The results of infrared spectroscopic (IR) analysis are shown in FIG. 7. In the Table, "2θ" indicates a diffraction angle (2θ°), and "Relative Intensity" indicates a relative intensity ratio ($I/I_0$). The relative intensity ratio is shown when the ratio is 1 or more.

TABLE 6

| 2θ | Relative Intensity |
|---|---|
| 5.1 | 100 |
| 10.5 | 1 |
| 10.9 | 2 |
| 14.0 | 2 |
| 15.3 | 8 |
| 16.4 | 2 |
| 16.8 | 2 |
| 19.4 | 2 |
| 20.4 | 3 |
| 21.4 | 2 |
| 21.9 | 3 |
| 23.9 | 1 |
| 24.9 | 1 |
| 25.5 | 2 |
| 26.1 | 1 |
| 28.1 | 1 |
| 30.7 | 1 |
| 34.7 | 1 |
| 35.4 | 1 |

As a result of measuring the L-ornithine content in the crystal by HPLC, the content was 53.6 wt %, which substantially coincided with the theoretical value (52.8 wt %) of a mono-ornithine salt. In addition, as a result of measuring the water amount contained in the crystal by the Karl-Fischer method, the content was 2.0 wt %.

Accordingly, it was found that the crystal is a crystal of ornithine salt nonhydrate of HMB. Various physical properties of the crystal acquired in Example 6 are shown in Table 7.

TABLE 7

| Water % | Ornithine content % | Melting point ° C. |
|---|---|---|
| 2.0 | 53.6 | 171.6 |

Example 7

Acquisition 2 of Crystal of Ornithine Salt Nonhydrate of HMB 4.6 L of the aqueous solution containing 280.3 g of the free HMB was obtained in the same manner as in Reference Example 1. 615 mL of an aqueous 510 g/L ornithine solution was added to the obtained solution to adjust the pH to 6.2. The obtained aqueous solution was concentrated under conditions of 50° C. and 15 mbar such that the weight of the concentrated solution becomes 696 g. 1.8 g of the seed crystal of ornithine salt nonhydrate of HMB obtained according to Example 5 was added thereto while maintaining the solution at room temperature, and thereby the crystal was precipitated. The crystal slurry was ripened for 24 hours at room temperature, and then subjected to centrifugal separation, and the crystal was then collected by filtration. The crystal was further vacuum-dried for 24 hours under conditions of 40° C. and 30 hPa, and therefore 180 g of a crystal was obtained.

As a result of measuring the L-ornithine content in the crystal by HPLC, the content was 51.6 wt %, which substantially coincided with the theoretical value (52.8 wt %) of a mono-ornithine salt. In addition, as a result of measuring the water amount contained in the crystal by the Karl-Fischer method, the content was 0.5 wt %.

Accordingly, it was found that the crystal is a crystal of ornithine salt nonhydrate of HMB. Various physical properties of the crystal acquired in Example 7 are shown in Table 8.

TABLE 8

| Water % | Ornithine content % | Melting point ° C. |
|---|---|---|
| 0.5 | 51.6 | 169-172 |

The results of powder X-ray diffraction of the crystal are shown in FIG. 8 and Table 9. In the Table, "2θ" indicates a diffraction angle (2θ°), and "Relative Intensity" indicates a relative intensity ratio ($I/I_0$). The relative intensity ratio is shown when the ratio is 2 or more.

TABLE 9

| 2θ | Relative Intensity |
|---|---|
| 4.9 | 68 |
| 5.2 | 66 |
| 5.5 | 100 |
| 10.9 | 6 |
| 15.5 | 7 |
| 15.9 | 3 |
| 16.4 | 20 |
| 17.4 | 2 |
| 19.2 | 4 |
| 20.4 | 3 |
| 20.8 | 4 |
| 21.3 | 6 |
| 21.8 | 6 |
| 22.2 | 7 |
| 22.8 | 2 |
| 23.5 | 3 |
| 23.9 | 5 |
| 24.5 | 2 |
| 24.9 | 2 |
| 25.4 | 2 |
| 25.8 | 2 |
| 27.2 | 3 |
| 33.3 | 3 |
| 33.6 | 2 |
| 34.3 | 2 |
| 35.9 | 3 |
| 36.1 | 2 |
| 36.7 | 2 |
| 38.5 | 2 |
| 41.0 | 2 |

When FIG. 8 which is a chart diagram of the crystal acquired in Example 7 was compared with FIG. 6 which is a chart diagram of the crystal acquired in Example 6, these do not coincide with each other. Accordingly, it was confirmed that the crystal has a different crystal form compared to the crystal obtained in Example 6.

Example 8

Measurement of Solubility

The crystals of arginine salt nonhydrate of HMB obtained in Example 3 and calcium salt hydrate of HMB (manufactured by Tokyo Chemical Industry Co., Ltd.) were added respectively at room temperature until they dissolved in water, and after keeping the solution for a sufficient time under stirring, the supernatant containing no crystal was sampled and measured for the HMB concentration by using HPLC. The measurement results are shown in Table 10.

TABLE 10

|  | Solubility (g/L) | Solubility (in terms of free form) (g/L) |
|---|---|---|
| Arginine salt nonhydrate of HMB | 829 | 335 |
| Calcium salt hydrate of HMB (*1) | 150 | 129 |

(*1): Purchased from Tokyo Chemical Industry Co., Ltd.

As shown in Table 10, it was found that the acquired crystal of arginine salt nonhydrate of HMB is greatly enhanced in the solubility in water, as compared to an existing calcium salt of HMB.

Example 9

Mixing of Crystals of Arginine Salt of HMB and Lysine Salt of HMB with Phosphate Buffer A 100 g/L solution, in terms of free form, was prepared using the crystal of arginine salt nonhydrate of HMB obtained in Example 3, the crystal of lysine salt nonhydrate of HMB obtained in Example 4, and calcium salt hydrate of HMB (manufactured by Tokyo Chemical Industry Co., Ltd.), and mixed with 0.2 M phosphate buffer (pH: 6.80) in an arbitrary mixing ratio. The solution after mixing was measured for the light transmittance (660 nm) to evaluate the presence or absence of insoluble salt formation. The results are shown in Table 11.

TABLE 11

| | Transmittance T % (660 nm) | | | |
| --- | --- | --- | --- | --- |
| | Mixing Ratio (Vol/Vol) (*1) | | | |
| | 0.01 | 0.17 | 0.33 | 0.57 |
| Arginine salt | — | 100 | 100 | 100 |
| Lysine salt | — | 100 | 100 | 100 |
| Calcium salt | 60 | 0.11 | 0.02 | 0 |

(*1) Vol/Vol = HMB 100 g/L aqueous solution (Vol)/0.2M phosphate buffer (Vol)

As shown in Table 11, it was found that in the mixing with the phosphate buffer, the existing calcium salt of HMB forms an insoluble salt but the acquired crystals of arginine salt nonhydrate of HMB and lysine salt nonhydrate of HMB do not form an insoluble salt.

Example 10

Mixing of Crystal of Arginine Salt of HMB and Glucose-Amino Acids-Electrolytes Infusion Solution The arginine salt nonhydrate of HMB obtained in Example 3 and calcium salt hydrate of HMB (manufactured by Tokyo Chemical Industry Co., Ltd.) were mixed with a glucose-amino acids-electrolytes infusion solution for peripheral vein nutrition [pH: about 6.7; Product Name: Aminofluid Infusion Solution (Otsuka Pharmaceutical Factory, Inc.)] to obtain 0, 0.11, 0.21 and 0.42 weight/volume % solutions at final concentration, respectively, in terms of free form. The light transmittance T % (660 nm) was measured by ultraviolet and visible spectrophotometer immediately after the mixing or 24 hours after being left at room temperature to evaluate the presence or absence of insoluble salt formation. The results are shown in Table 12.

TABLE 12

| | Transmittance T % (660 nm) | | | |
| --- | --- | --- | --- | --- |
| | T (%) Time after addition (h) | | | |
| HMB final concentration (weight/volume %) | 0 | 24 | 0 | 24 |
| | Calcium salt | | Arginine salt | |
| 0 | 100 | 100 | 100 | 100 |
| 0.11 | 100 | 70 | 100 | 100 |
| 0.21 | 90 | 28 | 100 | 100 |
| 0.42 | 65 | 20 | 100 | 100 |

As shown in Table 12, it was found that in the mixing with the Aminofluid infusion solution, the existing calcium salt of HMB forms an insoluble salt but the acquired arginine salt nonhydrate of HMB does not form an insoluble salt.

Example 11

Effect on Body Electrolyte when Glucose-Electrolytes Infusion Solution Containing Crystal of Arginine Salt of HMB is Administered The arginine salt nonhydrate of HMB obtained in Example 3 and calcium salt hydrate of HMB (manufactured by Tokyo Chemical Industry Co., Ltd.) were mixed with a glucose-electrolytes infusion solution [Product Name: SOLITA-T No. 3 Infusion Solution (AY Pharmaceuticals Co., Ltd.)] that does not contain phosphate ion to obtain 0 and 0.42 weight/volume % solutions at final concentration, respectively, in terms of free form. The solution was continuously administered to surgically stressed rats underwent intestinal tract scratch operation at a normal dose (240 mL/kg/day) for 3 days. On the final day of administration, urine was collected by 24-hour urine collection and measured for the urinary electrolyte concentration. The results are shown in Tables 13 and 14.

TABLE 13

| | Urinary calcium excretion amount (mg/day) | |
| --- | --- | --- |
| HMB final concentration | Urinary calcium excretion amount (mg/day) | |
| (weight/volume %) | Calcium salt | Arginine salt |
| 0 | 0.30 | 0.30 |
| 0.42 | 3.64 | 0.24 |

TABLE 14

| | Urinary phosphate excretion amount (mg/day) | |
| --- | --- | --- |
| HMB final concentration | Urinary phosphate excretion amount (mg/day) | |
| (weight/volume %) | Calcium salt | Arginine salt |
| 0 | 18.4 | 18.4 |
| 0.42 | 4.4 | 19.1 |

As shown in Tables 13 and 14, it was found that in the combined administration with the SOLITA-T No. 3 infusion solution, the existing calcium salt of HMB induces the increase in urinary calcium and the decrease in urinary phosphate excretion but the acquired crystal of arginine salt nonhydrate of HMB does not induce the above electrolyte abnormality.

Example 12

Sensory Evaluation Test 1
[Preparation of Beverage (1)]

6 g of ornithine salt nonhydrate of HMB obtained in Example 7, 4 g of maltitol (manufactured by Mitsubishi Shoji Foodtech Co., Ltd.), 120 μL of apple essence (manufactured by TAKATA KORYO CO., LTD.), 120 μL of sugar flavor (manufactured by Ogawa & Co., Ltd.), and 200 mg of aspartame (manufactured by AJINOMOTO CO., INC.) were added to 200 mL of water and dissolved. An appropriated amount of a citric acid (manufactured by MC Food Specialties Inc) was added to this solution, and after adjusting a pH to 3.70, each 100 mL was dispensed into a glass bottle, and an aluminum cap was put. The glass bottle was heated at 90° C. for 5 minutes, and then left to stand at room temperature to be cooled, and thereby Beverage (1) was produced. As a result of visually confirming the presence or absence of precipitation and turbidity immediately after being left to stand at room temperature, precipitation and turbidity were not found.

[Preparation of Comparative Beverage (1)]

Comparative Beverage (1) was prepared in the same manner as in Beverage (1) except that calcium salt of HMB (HMB Kyowa, manufactured by KYOWA HAKKO BIO CO., LTD.) used instead of ornithine salt nonhydrate of HMB. The presence or absence of precipitation and turbidity immediately after being left to stand at room temperature was visually confirmed. As a result, white precipitation was found in a large amount.

Eight panelists evaluated which one of Beverage (1) and Comparative Beverage (1) is preferably in flavor through a two-point discrimination test. As a result, eight out of eight evaluated that Beverage (1) is clearly preferable than Comparative Beverage (1) in flavor. From the result, it was found that the obtained ornithine salt of HMB has the excellent effect of enhancing the solubility and flavor compared to calcium salt of HMB.

Example 13

Sensory Evaluation Test 2
[Preparation of Beverage (2)]

6 g of arginine salt nonhydrate of HMB obtained in Example 3, 4 g of maltitol (manufactured by Mitsubishi Shoji Foodtech Co., Ltd.), 120 μL of black currant essence (manufactured by Ogawa & Co., Ltd.), 60 mg of molasses flavor (manufactured by Mitsui Sugar Co., Ltd.), and 200 mg of *stevia* (manufactured by B Food Science Co., Ltd.) were added to 200 mL of water and dissolved. An appropriated amount of 75% phosphate (manufactured by Taiyo Chemical Industry Co., Ltd.) was added to this solution, and after adjusting a pH to 3.70, each 100 mL was dispensed into a glass bottle, and an aluminum cap was put. The glass bottle was heated at 90° C. for 5 minutes, and then left to stand at room temperature to be cooled, and immediately after that, the presence or absence of precipitation and turbidity was visually confirmed. As a result, no precipitation and turbidity were found.

[Preparation of Comparative Beverage (2)]

Comparative Beverage (2) was prepared in the same manner as in Beverage (2) except that calcium salt of HMB (HMB Kyowa, manufactured by KYOWA HAKKO BIO CO., LTD.) used instead of arginine salt nonhydrate of HMB. The presence or absence of precipitation and turbidity immediately after being left to stand at room temperature was visually confirmed. As a result, white precipitation was found as same as before heating.

Eight panelists evaluated which one of Beverage (2) and Comparative Beverage (2) is preferably in flavor through a two-point discrimination test. As a result, eight out of eight evaluated that Beverage (2) is clearly preferable than Comparative Beverage (2) in flavor. From the result, it was found that the obtained arginine salt of HMB has the excellent effect of enhancing the solubility and flavor compared to calcium salt of HMB.

While the present invention has been described in detail and with reference to specific embodiments thereof, it will be apparent to one skilled in the art that various changes and modifications can be made therein without departing from the spirit and scope of the present invention. This application is based on Japanese Patent Application (Patent Application No. 2016-125280) filed on Jun. 24, 2016, the entirety of which is incorporated herein by way of reference. All references cited herein are incorporated herein in its entirety.

INDUSTRIAL APPLICABILITY

According to the present invention, a crystal of an amino acid salt of HMB nonhydrate, which is useful, for example, as a product, a raw material, an intermediate, or the like of health food, medicines, cosmetics, or the like, and a production method thereof are provided.

The invention claimed is:

1. A crystal of an amino acid salt of a 3-hydroxyisovaleric acid (HMB) wherein
   (i) the amino acid salt of HMB is an arginine salt of HMB, and in powder X-ray diffraction, the crystal has peaks at diffraction angles (2θ) of 7.5±0.2°, 14.5±0.2°, 15.1±0.2°, 19.2±0.2°, and 20.2±0.2°,
   (ii) the amino acid salt of HMB is a lysine salt of HMB, and in powder X-ray diffraction, the crystal has peaks at diffraction angles (2θ) of 8.5±0.2°, 17.0±0.2°, 18.1±0.2°, 18.5±0.2°, and 19.5±0.2°,
   (iii) the amino acid salt of HMB is an ornithine salt of HMB, and in powder X-ray diffraction, the crystal has peaks at diffraction angles (2θ) of 5.1±0.2°, 14.0±0.2°, 15.3±0.2°, 20.4±0.2°, and 21.9±0.2°, or
   (iv) the amino acid salt of HMB is an ornithine salt of HMB, and in powder X-ray diffraction, the crystal has peaks at diffraction angles (2θ) of 4.9±0.2°, 5.2±0.2°, 5.5±0.2°, 10.9±0.2° and 15.5±0.2°.

2. The crystal according to claim 1, wherein the amino acid salt of HMB is an arginine salt of HMB, and in powder X-ray diffraction, the crystal has peaks at diffraction angles (2θ) of 7.5±0.2°, 14.5±0.2°, 15.1±0.2°, 19.2±0.2°, and 20.2±0.2°.

3. The crystal according to claim 2, wherein in powder X-ray diffraction, the crystal further has peaks at diffraction angles (2θ) of 11.6±0.2°, 12.7±0.2°, 17.9±0.2°, 21.5±0.2°, and 23.3±0.2°.

4. The crystal according to claim 3, wherein in powder X-ray diffraction, the crystal further has peaks at diffraction angles (2θ) of 19.6±0.2°, 21.9±0.2°, 25.2±0.2°, 25.5±0.2°, and 33.6±0.2°.

5. The crystal according to claim 1, wherein the amino acid salt of HMB is a lysine salt of HMB, and in powder X-ray diffraction, the crystal has peaks at diffraction angles (2θ) of 8.5±0.2°, 17.0±0.2°, 18.1±0.2°, 18.5±0.2°, and 19.5±0.2°.

6. The crystal according to claim 5, wherein in powder X-ray diffraction, the crystal further has peaks at diffraction angles (2θ) of 22.2±0.2°, 25.5±0.2°, 25.8±0.2°, 26.6±0.2°, and 34.4±0.2°.

7. The crystal according to claim 6, wherein in powder X-ray diffraction, the crystal further has peaks at diffraction angles (2θ) of 4.8±0.2°, 20.4±0.2°, 31.0±0.2°, 33.8±0.2°, and 36.5±0.2°.

8. The crystal according to claim 1, wherein the amino acid salt of HMB is an ornithine salt of HMB, and in powder X-ray diffraction, the crystal has peaks at diffraction angles (2θ) of 5.1±0.2°, 14.0±0.2°, 15.3±0.2°, 20.4±0.2°, and 21.9±0.2°.

9. The crystal according to claim 8, wherein in powder X-ray diffraction, the crystal further has peaks at diffraction angles (2θ) of 16.4±0.2°, 16.8±0.2°, 19.4±0.2°, 21.4±0.2°, and 25.5±0.2°.

10. The crystal according to claim 9, wherein in powder X-ray diffraction, the crystal further has peaks at diffraction angles (2θ) of 10.9±0.2°.

11. A method for producing a crystal of an amino acid salt of 3-hydroxyisovaleric acid (HMB) according to claim 1, the method comprising:
    a step of dissolving an amorphous amino acid salt of HMB in a solvent containing alcohol, a step of precipitating a crystal of an amino acid salt of HMB by stirring or allowing the solvent to left stand, and a step of collecting a crystal of an amino acid salt of HMB from the solvent.

12. A method for producing a crystal of an amino acid salt of 3-hydroxyisovaleric acid (HMB) according to claim 1, the method comprising:
    a step of concentrating an aqueous HMB solution containing an amino acid-containing compound and having a pH of 2.5 to 11.0 to precipitate a crystal of an amino acid salt of HMB, and a step of collecting a crystal of an amino acid salt of HMB from the aqueous solution.

13. The production method according to claim 12, wherein the step of precipitating a crystal of an amino acid salt of HMB includes a step of adding or adding dropwise at least one solvent selected from the group consisting of alcohol, nitrile, and ketone.

14. The production method according to claim 11, wherein the alcohol is at least one alcohol selected from the group consisting of C1 to C6 alcohols.

15. The production method according to claim 13, wherein the nitrile is acetonitrile.

16. The production method according to claim 13, wherein the ketone is at least one ketone selected from the group consisting of acetone, methyl ethyl ketone, methyl isobutyl ketone, and diethyl ketone.

17. The crystal according to claim 1, wherein the amino acid salt of HMB is an ornithine salt of HMB, and in powder X-ray diffraction, the crystal has peaks at diffraction angles (2θ) of 4.9±0.2°, 5.2±0.2°, 5.5±0.2°, 10.9±0.2°, 9±0.2° and 15.5±0.2°.

18. The crystal according to claim 17, wherein in powder X-ray diffraction, the crystal further has peaks at diffraction angles (2θ) of 15.9±0.2°, 16.4±0.2°, 17.4±0.2°, 19.2±0.2°, and 20.4±0.2°.

19. The crystal according to claim 18, wherein in powder X-ray diffraction, the crystal further has peaks at diffraction angles (2θ) of 20.8±0.2°, 21.3±0.2°, 21.8±0.2°, 22.2±0.2°, and 22.8±0.2°.

20. The production method according to claim 12, wherein the alcohol is at least one alcohol selected from the group consisting of C1 to C6 alcohols.

* * * * *